United States Patent
Popi

(10) Patent No.: US 7,605,315 B1
(45) Date of Patent: Oct. 20, 2009

(54) PLANTS AND SEEDS OF HYBRID CORN VARIETY CH675395

(75) Inventor: Jon Popi, London (CA)

(73) Assignee: Monsanto Technology LLC, St. Louis, MO (US)

( * ) Notice: Subject to any disclaimer, the term of this patent is extended or adjusted under 35 U.S.C. 154(b) by 11 days.

(21) Appl. No.: 12/117,935

(22) Filed: May 9, 2008

(51) Int. Cl.
*A01H 1/00* (2006.01)
*A01H 1/02* (2006.01)
*A01H 5/00* (2006.01)
*A01H 5/10* (2006.01)

(52) U.S. Cl. .................... 800/320.1; 800/260; 800/275; 800/278; 800/298; 800/295; 800/300; 800/300.1; 800/302; 800/301; 435/412; 435/424; 435/468; 435/430.1

(58) Field of Classification Search ........................ None
See application file for complete search history.

(56) References Cited

U.S. PATENT DOCUMENTS

| | | | |
|---|---|---|---|
| 4,517,763 A | 5/1985 | Beversdorf et al. | 47/58 |
| 4,658,084 A | 4/1987 | Beversdorf et al. | 800/1 |
| 4,658,085 A | 4/1987 | Beversdorf et al. | 800/1 |
| 4,677,246 A | 6/1987 | Armond et al. | 800/1 |
| 4,731,499 A | 3/1988 | Puskaric et al. | 800/1 |
| 5,276,263 A | 1/1994 | Foley | 800/200 |
| 5,276,266 A | 1/1994 | Eggerling | 800/200 |
| 5,523,520 A | 6/1996 | Hunsperger et al. | 800/200 |
| 5,773,683 A | 6/1998 | Foley | 800/200 |
| 6,433,261 B2 | 8/2002 | Hotchkiss | 800/320.1 |
| 6,693,232 B1 | 2/2004 | Bergemann | 800/320.1 |
| 6,852,915 B2 | 2/2005 | Johnson | 800/320.1 |
| 7,157,625 B1 | 1/2007 | Popi et al. | 800/320.1 |
| 7,317,155 B1 * | 1/2008 | Popi | 800/320.1 |

OTHER PUBLICATIONS

Armstrong et al., "Establishment and maintenance of friable embryogenic maize callus and the involvement of L-proline," *Planta*, 164:207-214, 1985.
U.S. Appl. No. 12/115,437, filed May 5, 2008, Popi.
Duvick, "Genetic Contributions to Yield Gains of U.S. Hybrid Maize, 1930 to 1980," Gen/etic/Contributions to Yield Gains of Five Major Crop Plants: Proceedings of a Symposium sponsored by Div. C-1, Crop Science Society of America, Dec. 2, 1981 in Atlanta, Georgia; W.R. Fehr, Crop Science Society of America and American Society of Agronomy, Madison, Wisconsin, pp. 15-47.
Eshed et al., "Less-than-additive epistatic interactions of quantitative trait loci in tomato," *Genetic*, 143:1807-1817, 1996.
Falkner et al., "Lax leaf maize: cell wall composition and nutritional value," *J. Sci. Food Agric.*, 80:255-262, 2000.
Fehr (ed.), In: Principles of Cultivar Development, vol. 1: Theory and Technique, pp. 360-376, 1987.
Hallauer et al., "Corn breeding," In: Corn and Corn Improvement, Sprague et al. (Eds.), Madison, Wisconsin, Ch. 8, pp. 463-564, 1988.
Kraft et al., "Linkage disequilibrium and fingerprinting in sugar beet," *Theor Appl Genet*, 101:323-326, 2000.
Krakowsky et al., "Quantitative trait loci for cell wall components in recombinant inbred lines of maize (*Zea mays* L.) II: leaf sheath tissue," *Theor Appl Genet* 112:717-726, 2006.
Larson et al., "Corn Production," In: Corn and Corn Improvement, G.F. Sprague (Ed.), No. 18 in Agronomy Series, American Society of Agronomy, Inc., Madison, Wisconsin, pp. 625-669, 1977.
Meghji et al., "Inbreeding depression, inbred and hybrid grain yields, and other traits of maize genotypes representing three eras," *Crop Science*, 24:545-549, 1984.
Poehlman et al. (eds), Breeding Field Crops, 4th Ed., pp. 172-175, 1995.
Poehlman, *Breeding Field Crops*, 3rd ed., AVI Publishing Company, Westport, Connecticut, pp. 469-481, 1987.
Rieger et al., Glossary of Genetics and Cytogenetics, Classical and Molecular, Springer-Verlag, Berlin, p. 116, 1976.
Sprague et al., "Corn Breeding," In: Corn and Corn Improvements, G.F. Sprague (Ed.), No. 18 in Agronomy Series, American Society of Agronomy, Inc., Madison, Wisconsin, pp. 305-362, 1977.
Troyer, "A retrospective view of corn genetic resources," *Journal of Heredity*, 81:17-24, 1990.
Wych, "Production of hybrid seed corn," In: Corn and Corn Improvement, Sprague et al. (Eds.), Madison, Wisconsin, Ch. 9, pp. 565-607, 1988.

* cited by examiner

*Primary Examiner*—Medina A Ibrahim
(74) *Attorney, Agent, or Firm*—Sonnenschein Nath & Rosenthal LLP

(57) ABSTRACT

According to the invention, there is provided seed and plants of the hybrid corn variety designated CH675395. The invention thus relates to the plants, seeds and tissue cultures of the variety CH675395, and to methods for producing a corn plant produced by crossing a corn plant of variety CH675395 with itself or with another corn plant, such as a plant of another variety. The invention further relates to genetic complements of plants of variety CH675395.

26 Claims, No Drawings

PLANTS AND SEEDS OF HYBRID CORN VARIETY CH675395

BACKGROUND OF THE INVENTION

1. Field of the Invention

The present invention relates generally to the field of corn breeding. In particular, the invention relates to corn seed and plants of the hybrid variety designated CH675395, and derivatives and tissue cultures thereof.

2. Description of Related Art

The goal of field crop breeding is to combine various desirable traits in a single variety/hybrid. Such desirable traits include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Corn plants (*Zea mays* L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ear shoot.

Plants that have been self-pollinated and selected for type over many generations become homozygous at almost all gene loci and produce a uniform population of true breeding progeny, a homozygous plant. A cross between two such homozygous plants produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform corn plant hybrids requires the development of homozygous inbred plants, the crossing of these inbred plants, and the evaluation of the crosses. Pedigree breeding and recurrent selection are examples of breeding methods used to develop hybrid parent plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

North American farmers plant tens of millions of acres of corn at the present time and there are extensive national and international commercial corn breeding programs. A continuing goal of these corn breeding programs is to develop corn hybrids that are based on stable inbred plants and have one or more desirable characteristics. To accomplish this goal, the corn breeder must select and develop superior inbred parental plants.

SUMMARY OF THE INVENTION

In one aspect, the present invention provides a corn plant of the hybrid variety designated CH675395. Also provided are corn plants having all the physiological and morphological characteristics of the hybrid corn variety CH675395. A hybrid corn plant of the invention may further comprise a cytoplasmic or nuclear factor that is capable of conferring male sterility or otherwise preventing self-pollination, such as by self-incompatibility. Parts of the corn plant of the present invention are also provided, for example, pollen obtained from a hybrid plant and an ovule of the hybrid plant. The invention also concerns seed of the hybrid corn variety CH675395. The hybrid corn seed of the invention may be provided as a population of corn seed of the variety designated CH675395.

In another aspect of the invention, the hybrid corn variety CH675395 is provided comprising an added desired trait. The desired trait may be a genetic locus that is a dominant or recessive allele. In certain embodiments of the invention, the genetic locus confers traits such as, for example, male sterility, waxy starch, herbicide resistance, insect resistance, resistance to bacterial, fungal, nematode or viral disease, and altered fatty acid, phytate or carbohydrate metabolism. The genetic locus may be a naturally occurring corn gene introduced into the genome of a parent of the variety by backcrossing, a natural or induced mutation, or a transgene introduced through genetic transformation techniques. When introduced through transformation, a genetic locus may comprise one or more transgenes integrated at a single chromosomal location.

In yet another aspect of the invention, a hybrid corn plant of the variety designated CH675395 is provided, wherein a cytoplasmically-inherited trait has been introduced into said hybrid plant. Such cytoplasmically-inherited traits are passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and continue to be male sterile in the next generation. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmically inherited trait may be a naturally occurring maize trait or a trait introduced through genetic transformation techniques.

In another aspect of the invention, a tissue culture of regenerable cells of a plant of variety CH675395 is provided. The tissue culture will preferably be capable of regenerating plants capable of expressing all of the physiological and morphological characteristics of the variety, and of regenerating plants having substantially the same genotype as other plants of the variety. Examples of some of the physiological and morphological characteristics of the variety CH675395 include characteristics related to yield, maturity, and kernel quality, each of which is specifically disclosed herein. The regenerable cells in such tissue cultures will preferably be derived from embryos, meristematic cells, immature tassels, microspores, pollen, leaves, anthers, roots, root tips, silk, flowers, kernels, ears, cobs, husks, or stalks, or from callus or protoplasts derived from those tissues. Still further, the present invention provides corn plants regenerated from the tissue cultures of the invention, the plants having all the physiological and morphological characteristics of variety CH675395.

In still another aspect, the invention provides a method of producing hybrid corn seed comprising crossing a plant of variety I325350 with a plant of variety CV646435. In a cross, either parent may serve as the male or female. Processes are also provided for producing corn seeds or plants, which processes generally comprise crossing a first parent corn plant with a second parent corn plant, wherein at least one of the first or second parent corn plants is a plant of the variety designated CH675395. In such crossing, either parent may serve as the male or female parent. These processes may be further exemplified as processes for preparing hybrid corn seed or plants, wherein a first hybrid corn plant is crossed with a second corn plant of a different, distinct variety to provide a hybrid that has, as one of its parents, the hybrid corn plant variety CH675395. In these processes, crossing will result in the production of seed. The seed production occurs regardless of whether the seed is collected or not.

In one embodiment of the invention, the first step in "crossing" comprises planting, preferably in pollinating proximity, seeds of a first and second parent corn plant, and preferably, seeds of a first corn plant and a second, distinct corn plant. Where the plants are not in pollinating proximity, pollination can nevertheless be accomplished by transferring a pollen or tassel bag from one plant to the other as described below.

A second step comprises cultivating or growing the seeds of said first and second parent corn plants into plants that bear flowers (corn bears both male flowers (tassels) and female flowers (silks) in separate anatomical structures on the same plant). A third step comprises preventing self-pollination of the plants, i.e., preventing the silks of a plant from being fertilized by any plant of the same variety, including the same plant. This is preferably done by emasculating the male flowers of the first or second parent corn plant, (i.e., treating or manipulating the flowers so as to prevent pollen production, in order to produce an emasculated parent corn plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step may comprise allowing cross-pollination to occur between the first and second parent corn plants. When the plants are not in pollinating proximity, this is done by placing a bag, usually paper or glassine, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place. Yet another step comprises harvesting the seeds from at least one of the parent corn plants. The harvested seed can be grown to produce a corn plant or hybrid corn plant.

The present invention also provides corn seed and plants produced by a process that comprises crossing a first parent corn plant with a second parent corn plant, wherein at least one of the first or second parent corn plants is a plant of the variety designated CH675395. In one embodiment of the invention, corn seed and plants produced by the process are first generation hybrid corn seed and plants produced by crossing an inbred with another, distinct inbred. The present invention further contemplates seed of an $F_1$ hybrid corn plant. Therefore, certain exemplary embodiments of the invention provide an $F_1$ hybrid corn plant and seed thereof, specifically the hybrid variety designated CH675395.

Such a plant can be analyzed by its "genetic complement." This term is used to refer to the aggregate of nucleotide sequences, the expression of which defines the phenotype of, for example, a corn plant, or a cell or tissue of that plant. A genetic complement thus represents the genetic make up of an cell, tissue or plant. The invention thus provides corn plant cells that have a genetic complement in accordance with the corn plant cells disclosed herein, and plants, seeds and diploid plants containing such cells.

Plant genetic complements may be assessed by genetic marker profiles, and by the expression of phenotypic traits that are characteristic of the expression of the genetic complement, e.g., marker typing profiles. It is known in the art that such complements may also be identified by marker types including, but not limited to, SSRs, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

DETAILED DESCRIPTION OF THE INVENTION

I. Definitions of Plant Characteristics

Barren Plants: Plants that are barren, i.e., lack an ear with grain, or have an ear with only a few scattered kernels.

Cg: *Colletotrichum graminicola* rating. Rating times 10 is approximately equal to percent total plant infection.

CLN: Corn Lethal Necrosis (combination of Maize Chlorotic Mottle Virus and Maize Dwarf Mosaic virus) rating: numerical ratings are based on a severity scale where 1=most resistant to 9=susceptible.

Cn: *Corynebacterium nebraskense* rating. Rating times 10 is approximately equal to percent total plant infection.

Cz: *Cercospora zeae-maydis* rating. Rating times 10 is approximately equal to percent total plant infection.

Dgg: *Diatraea grandiosella* girdling rating (values are percent plants girdled and stalk lodged).

Dropped Ears: Ears that have fallen from the plant to the ground.

Dsp: *Diabrotica* species root ratings (1=least affected to 9=severe pruning).

Ear-Attitude: The attitude or position of the ear at harvest scored as upright, horizontal, or pendant.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Diameter: The average diameter of the ear at its midpoint.

Ear-Dry Husk Color: The color of the husks at harvest scored as buff, red, or purple.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks. Minimum value no less than zero.

Ear-Husk Opening: An evaluation of husk tightness at harvest scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the sum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

Early Stand: The percent of plants that emerge from the ground as determined in the early spring.

ER: Ear rot rating (values approximate percent ear rotted).

Final Stand Count: The number of plants just prior to harvest.

GDUs: Growing degree units which are calculated by the Barger Method, where the heat units for a 24-h period are calculated as GDUs=[(Maximum daily temperature+Minimum daily temperature)/2]−50. The highest maximum daily temperature used is 86° F. and the lowest minimum temperature used is 50° F.

GDUs to Shed: The number of growing degree units (GDUs) or heat units required for a variety to have approximately 50% of the plants shedding pollen as measured from time of planting. GDUs to shed is determined by summing the individual GDU daily values from planting date to the date of 50% pollen shed.

GDUs to Silk: The number of growing degree units for a variety to have approximately 50% of the plants with silk emergence as measured from time of planting. GDUs to silk is determined by summing the individual GDU daily values from planting date to the date of 50% silking.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Hm: *Helminthosporium maydis* race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: Chlorotic-lesion type resistance. +=indicates the presence of Ht chlorotic-lesion type resistance; −=indicates absence of Ht chlorotic-lesion type resistance; and +/−=indicates segregation of Ht chlorotic-lesion type resistance. Rating times 10 is approximately equal to percent total plant infection.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow, or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent total plant infection.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination. Rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

LSS: Late season standability (values times 10 approximate percent plants lodged in disease evaluation plots).

Moisture: The moisture of the grain at harvest.

On1: *Ostrinia nubilalis* 1st brood rating (1=resistant to 9=susceptible).

On2: *Ostrinia nubilalis* 2nd brood rating (1=resistant to 9=susceptible).

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale, where 1 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 1 equals best.

STR: Stalk rot rating (values represent severity rating of 1=25% of inoculated internode rotted to 9=entire stalk rotted and collapsed).

SVC: Southeastern Virus Complex (combination of Maize Chlorotic Dwarf Virus and Maize Dwarf Mosaic Virus) rating; numerical ratings are based on a severity scale where 1=most resistant to 9=susceptible (1988 reactions are largely Maize Dwarf Mosaic Virus reactions).

Tassel-Anther Color: The color of the anthers at 50% pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50% shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: Weight of the grain in pounds for a given volume (bushel) adjusted to 15.5% moisture.

Yield: Yield of grain at harvest adjusted to 15.5% moisture.

II. Other Definitions

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Crossing: The pollination of a female flower of a corn plant, thereby resulting in the production of seed from the flower.

Cross-pollination: Fertilization by the union of two gametes from different plants.

Diploid: A cell or organism having two sets of chromosomes.

Emasculate: The removal of plant male sex organs or the inactivation of the organs with a chemical agent or a cytoplasmic or nuclear genetic factor conferring male sterility.

$F_1$ Hybrid: The first generation progeny of the cross of two plants.

Genetic Complement: An aggregate of nucleotide sequences, the expression of which sequences defines the phenotype in corn plants, or components of plants including cells or tissue.

Genotype: The genetic constitution of a cell or organism.

Haploid: A cell or organism having one set of the two sets of chromosomes in a diploid.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing wherein essentially all of the desired morphological and physiological characteristics of an inbred are recovered in addition to the characteristics conferred by the single locus transferred into the inbred via the backcrossing technique. A single locus may comprise one gene, or in the case of transgenic plants, one or more transgenes integrated into the host genome at a single site (locus).

Tissue Culture: A composition comprising isolated cells of the same or a different type or a collection of such cells organized into parts of a plant.

Transgene: A genetic sequence which has been introduced into the nuclear or chloroplast genome of a corn plant by a genetic transformation technique.

III. Variety Descriptions

In accordance with one aspect of the present invention, there is provided a novel hybrid corn plant variety designated CH675395. Hybrid variety CH675395 was produced from a cross of the inbred varieties designated I325350 and CV646435. The inbred parents have been self-pollinated and ear-rowed a sufficient number of generations with careful attention paid to uniformity of plant type to show uniformity and stability within the limits of environmental influence.

In accordance with one aspect of the invention, there is provided a corn plant having the physiological and morphological characteristics of corn plant CH675395. An analysis of such morphological traits was carried out, the results of which are presented in Table 1.

TABLE 1

Morphological Traits for Hybrid Variety CH675395

| | CHARACTERISTIC | VALUE |
|---|---|---|
| 1. | STALK | |
| | Plant Height cm. | 247.2 |
| | Ear Height cm. | 77.5 |
| | Anthocyanin | Absent |
| | Nodes With Brace Roots | 1.2 |
| | Brace Root Color | Faint |
| | Internode Direction | Zig-Zag |
| | Internode Length cm. | 20.5 |
| 2. | LEAF | |
| | Color | Dark Green |
| | Length cm. | 76.3 |

TABLE 1-continued

Morphological Traits for Hybrid Variety CH675395

| | CHARACTERISTIC | VALUE |
|---|---|---|
| | Width cm. | 8.9 |
| | Sheath Anthocyanin | Absent |
| | Sheath Pubescence | Heavy |
| | Marginal Waves | Moderate |
| | Longitudinal Creases | Moderate |
| 3. | TASSEL | |
| | Length cm. | 43.8 |
| | Spike Length cm. | 24.2 |
| | Peduncle Length cm. | 6.8 |
| | Branch Number | 8.0 |
| | Anther Color | Salmon |
| | Glume Color | Green |
| | Glume Band | Absent |
| 4. | EAR | |
| | Silk Color | Yellow |
| | Number Per Stalk | 1.0 |
| | Length cm. | 16.2 |
| | Diameter cm. | 4.1 |
| | Shank Length cm. | 14.6 |
| | Husk Bract | Short |
| | Husk Cover cm. | 3.1 |
| | Husk Color Fresh | Green |
| | Cob Diameter cm. | 2.2 |
| | Shelling Percent | 90.1 |
| 5. | KERNEL | |
| | Row Number | 13.0 |
| | Number Per Row | 36.0 |
| | Length (depth) mm. | 11.8 |
| | Width mm. | 8.4 |
| | Thickness | 3.9 |
| | Endosperm Type | Normal |

*These are typical values. Values may vary due to environment. Other values that are substantially equivalent are also within the scope of the invention.

*These are typical values. Values may vary due to environment. Other values that are substantially equivalent are also within the scope of the invention.

During the development of a hybrid plant detailed evaluations of the phenotype are made including formal comparisons with other commercially successful hybrids. Because the corn is grown in close proximity, environmental factors that affect gene expression, such as moisture, temperature, sunlight, and pests, are minimized. For a decision to be made to commercialize a hybrid, it is not necessary that the hybrid be better than all other hybrids. Rather, significant improvements must be shown in at least some traits that would create improvements in some niches. Examples of such comparative performance data for the hybrid corn plant CH675395 are set forth herein below in Table 2.

TABLE 2

Comparison of CH675395 With Selected Hybrid Varieties

| HYBRID | YLD BU | MST PTS | STL % | RTL % | SV RAT | PHT INCH | EHT INCH | SG RAT | TST LBS |
|---|---|---|---|---|---|---|---|---|---|
| CH675395 | 149.40 | 8.02 | 3.92 | .00 | 3.00 | 84.71 | 33.50 | 6.19 | 61.03 |
| DKC 29-97 | 143.04 | 7.30 | 4.71 | .14 | 3.25 | 78.14 | 36.00 | 7.69 | 60.56 |
| DIFF. | 6.36 | .72 | −.79 | −.14 | −.25 | 6.57 | −2.50 | −1.50 | .46 |
| SIG. | + | ** | | | | ** | * | ** | * |
| CH675395 | 149.40 | 8.02 | 3.92 | .00 | 3.00 | 84.71 | 33.50 | 6.19 | 61.03 |
| DKC 29-98 | 150.81 | 7.43 | 4.40 | 2.62 | 3.67 | 79.93 | 35.29 | 7.31 | 60.50 |
| DIFF. | −1.42 | .58 | −.48 | −2.62 | −.67 | 4.79 | −1.79 | −1.13 | .52 |
| SIG. | | * | | + | * | * | | * | * |
| CH675395 | 147.73 | 7.96 | 4.20 | .00 | 3.20 | 84.71 | 33.50 | 6.19 | 61.07 |
| DKC 30-02 | 139.57 | 7.45 | 4.28 | .28 | 4.40 | 84.43 | 36.07 | 5.44 | 61.12 |

TABLE 2-continued

Comparison of CH675395 With Selected Hybrid Varieties

| HYBRID | YLD BU | MST PTS | STL % | RTL % | SV RAT | PHT INCH | EHT INCH | SG RAT | TST LBS |
|---|---|---|---|---|---|---|---|---|---|
| DIFF. | 8.16 | .51 | −.08 | −.28 | −1.20 | .29 | −2.57 | .75 | −.05 |
| SIG. | + | * | | | * | | + | + | |

Significance levels are indicated as:
+ = 10%,
* = 5%,
** = 1%
LEGEND ABBREVIATIONS:
HYBD = Hybrid
NTEST = Research/FACT
SI % C = Selection Index (percent of check)
YLD BU/A = Yield (bushels/acre)
MST PTS = Moisture
STL % = Stalk Lodging (percent)
RTL % = Root Lodging (percent)
DRP % = Dropped Ears (percent)
FLSTD % M = Final Stand (percent of test mean)
SV RAT = Seedling Vigor Rating
ELSTD % M = Early Stand (percent of test mean)
PHT INCH = Plant Height (inches)
EHT INCH = Ear Height (inches)
BAR % = Barren Plants (percent)
SG RAT = Staygreen Rating
TST LBS = Test Weight (pounds)
FGDU = GDUs to Shed
ESTR DAYS = Estimated Relative Maturity (days)

In accordance with another aspect of the present invention, there is provided a corn plant having the physiological and morphological characteristics of corn plant CV646435. A description of the physiological and morphological characteristics of corn plant CV646435 is presented in Table 3.

TABLE 3

Physiological and Morphological Traits for Corn Variety CV646435

| | CHARACTERISTIC | VALUE |
|---|---|---|
| 1. | STALK | |
| | Plant Height (cm.) | 178.4 |
| | Ear Height (cm) | 60.7 |
| | Anthocyanin | Weak |
| | Brace Root Color | Absent |
| | Nodes With Brace Roots | 1.4 |
| | Internode Direction | Zig-Zag |
| | Internode Length cm. | 12.6 |
| 2. | LEAF | |
| | Color | Dark Green |
| | Length cm. | 59.3 |
| | Width cm. | 7.3 |
| | Sheath Anthocyanin | Weak |
| | Sheath Pubescence | Light |
| | Marginal Waves | Moderate |
| | Longitudinal Creases | Few |
| 3. | TASSEL | |
| | Length cm. | 34.9 |
| | Spike Length cm. | 15.7 |
| | Peduncle Length cm. | 6.3 |
| | Branch Number | 15.0 |
| | Anther Color | Salmon |
| | Glume Color | Light Red |
| | Glume Band | Absent |
| 4. | EAR | |
| | Silk Color | Red |
| | Number Per Stalk | 1.0 |
| | Position (attitude) | Upright |
| | Length cm. | 10.8 |
| | Shape | Semi-Conical |
| | Diameter cm. | 3.4 |
| | Shank Length cm. | 6.3 |

TABLE 3-continued

Physiological and Morphological Traits for Corn Variety CV646435

| | CHARACTERISTIC | VALUE |
|---|---|---|
| | Husk Bract | Short |
| | Husk Cover cm. | 5.3 |
| | Husk Opening | Very Tight |
| | Husk Color Fresh | Green |
| | Husk Color Dry | Buff |
| | Cob Diameter cm. | 1.9 |
| | Cob Color | Red |
| | Shelling Percent | 89.4 |
| 5. | KERNEL | |
| | Row Number | 14.0 |
| | Number Per Row | 27.4 |
| | Row Direction | Straight |
| | Type | Dent |
| | Cap Color | Yellow |
| | Side Color | Deep Yellow |
| | Length (depth) mm. | 9.8 |
| | Width mm. | 7.7 |
| | Thickness | 4.2 |
| | Endosperm Type | Normal |
| | Endosperm Color | Yellow |

*These are typical values. Values may vary due to environment. Other values that are substantially equivalent are also within the scope of the invention.

IV. Deposit Information

A deposit of at least 2500 seeds of inbred parent plant varieties I325350 (U.S. Pat. No. 7,157,625, the entire disclosure of which is incorporated herein by reference) and CV646435 (U.S. application Ser. No. 12/115,437, filed May 5, 2008, the entire disclosure of which is incorporated herein by reference) has been made with the American Type Culture Collection (ATCC), 10801 University Boulevard, Manassas, Va. 20110-2209 USA, and assigned ATCC Accession Nos. PTA-7866, and PTA-10243, respectively. The seeds were deposited with the ATCC on Sep. 13, 2006, and Jul. 27, 2009, respectively. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent or under the Plant Variety Protection Act (7 U.S.C. 2321 et seq.).

V. Further Embodiments of the Invention

In certain further aspects, the invention provides plants modified to include at least a first desired trait. Such plants may, in one embodiment, be developed by a plant breeding technique called backcrossing, wherein essentially all of the desired morphological and physiological characteristics of a variety are recovered in addition to a genetic locus transferred into the hybrid via the backcrossing technique. By essentially all of the desired morphological and physiological characteristics, it is meant that all of the characteristics of a plant are recovered that are otherwise present when compared in the same environment, other than an occasional variant trait that might arise during backcrossing or direct introduction of a transgene. In one embodiment, such traits may be determined, for example, relative to the traits listed in Table 1 as determined at the 5% significance level when grown under the same environmental conditions.

Backcrossing methods can be used with the present invention to improve or introduce a trait in a hybrid via modification of its inbred parent(s). The term backcrossing as used herein refers to the repeated crossing of a hybrid progeny back to one of the parental corn plants for that hybrid. The parental corn plant which contributes the locus or loci for the desired trait is termed the nonrecurrent or donor parent. This terminology refers to the fact that the nonrecurrent parent is used one time in the backcross protocol and therefore does not recur.

The parental corn plant to which the locus or loci from the nonrecurrent parent are transferred is known as the recurrent parent as it is used for several rounds in the backcrossing protocol (Poehlman et al., 1995; Fehr, 1987; Sprague and Dudley, 1988). In a typical backcross protocol, the original parent hybrid of interest (recurrent parent) is crossed to a second variety (nonrecurrent parent) that carries the genetic locus of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the transferred locus from the nonrecurrent parent. The backcross process may be accelerated by the use of genetic markers, such as SSR, RFLP, SNP or AFLP markers to identify plants with the greatest genetic complement from the recurrent parent.

The selection of a suitable recurrent parent is an important step for a successful backcrossing procedure. The goal of a backcross protocol is to add or substitute one or more new traits in the original inbred and hybrid progeny therefrom. To accomplish this, a genetic locus of the recurrent parent is modified or substituted with the desired locus from the nonrecurrent parent, while retaining essentially all of the rest of the desired genetic, and therefore the desired physiological and morphological constitution of the original plant. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, waxy starch, herbicide resistance, resistance for bacterial, fungal, or viral disease, insect resistance, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where a genetic locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

Many useful traits are those which are introduced by genetic transformation techniques. Methods for the genetic transformation of corn are known to those of skill in the art. For example, methods which have been described for the genetic transformation of corn include electroporation (U.S. Pat. No. 5,384,253), electrotransformation (U.S. Pat. No. 5,371,003), microprojectile bombardment (U.S. Pat. No. 5,550,318; U.S. Pat. No. 5,736,369, U.S. Pat. No. 5,538,880; and PCT Publication WO 95/06128), *Agrobacterium*-mediated transformation (U.S. Pat. No. 5,591,616 and E.P. Publication EP672752), direct DNA uptake transformation of protoplasts (Omirulleh et al., 1993) and silicon carbide fiber-mediated transformation (U.S. Pat. No. 5,302,532 and U.S. Pat. No. 5,464,765).

It is understood to those of skill in the art that a transgene need not be directly transformed into a plant, as techniques for the production of stably transformed corn plants that pass single loci to progeny by Mendelian inheritance is well known in the art. Such loci may therefore be passed from parent plant to progeny plants by standard plant breeding techniques that are well known in the art.

A. Male Sterility

Examples of genes conferring male sterility include those disclosed in U.S. Pat. No. 3,861,709, U.S. Pat. No. 3,710,511, U.S. Pat. No. 4,654,465, U.S. Pat. No. 5,625,132, and U.S. Pat. No. 4,727,219, each of the disclosures of which are specifically incorporated herein by reference in their entirety. Male sterility genes can increase the efficiency with which hybrids are made, in that they eliminate the need to physically emasculate the corn plant used as a female in a given cross.

Where one desires to employ male-sterility systems with a corn plant in accordance with the invention, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the corn plant is utilized, e.g., for silage, but in most cases, the seeds will be deemed the most valuable portion of the crop, so fertility of the hybrids in these crops must be restored. Therefore, one aspect of the current invention concerns the hybrid corn plant CH675395 comprising a genetic locus capable of restoring male fertility in an otherwise male-sterile plant. Examples of male-sterility genes and corresponding restorers which could be employed with the plants of the invention are well known to those of skill in the art of plant breeding and are disclosed in, for instance, U.S. Pat. No. 5,530,191; U.S. Pat. No. 5,689,041; U.S. Pat. No. 5,741,684; and U.S. Pat. No. 5,684,242, the disclosures of which are each specifically incorporated herein by reference in their entirety.

B. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., (1988); Gleen et al., (1992); and Miki et al., (1990).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al. DeGreef et al., (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acct-S1, Accl-S2 and Acct-S3 genes described by Marshall et al., (1992).

Genes are also known conferring resistance to a herbicide that inhibits photosynthesis, such as a triazine (psbA and gs+ genes) and a benzonitrile (nitrilase gene). Przibilla et al., (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., (1992).

C. Waxy Starch

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits additional progeny testing, for example growing additional generations such as the BC1S1, may be required to determine which plants carry the recessive gene.

D. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., (1994) (cloning of the tomato Cf-9 gene for resistance to *Cladosporium fulvum*); Martin et al., (1993) (tomato Pto gene for resistance to *Pseudomonas syringae* pv.); and Mindrinos et al., (1994) (*Arabidopsis* RSP2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al., (1993), who show that transgenic plants expressing recombinant antibody genes are protected from virus attack.

Logemann et al., (1992), for example, disclose transgenic plants expressing a barley ribosome-inactivating gene have an increased resistance to fungal disease.

E. Insect Resistance

One example of an insect resistance gene includes a *Bacillus thuringiensis* protein, a derivative thereof or a synthetic polypeptide modeled thereon. See, for example, Geiser et al., (1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (1987) (nucleotide sequence of rice cysteine proteinase inhibitor), Huub et al., (1993) (nucleotide sequence of cDNA encoding tobacco proteinase inhibitor I), and Sumitani et al., (1993) (nucleotide sequence of *Streptomyces nitrosporeus* α-amylase inhibitor).

An insect-specific hormone or pheromone may also be used. See, for example, the disclosure by Hammock et al., (1990), of baculovirus expression of cloned juvenile hormone esterase, an inactivator of juvenile hormone.

Still other examples include an insect-specific antibody or an immunotoxin derived therefrom and a developmental-arrestive protein. See Taylor et al., (1994), who described enzymatic inactivation in transgenic tobacco via production of single-chain antibody fragments.

F. Modified Fatty Acid, Phytate and Carbohydrate Metabolism

Genes may be used conferring modified fatty acid metabolism. For example, stearyl-ACP desaturase genes may be used. See Knutzon et al., (1992). Various fatty acid desaturases have also been described, such as a *Saccharomyces cerevisiae* OLE1 gene encoding Δ9 fatty acid desaturase, an enzyme which forms the monounsaturated palmitoleic (16:1) and oleic (18:1) fatty acids from palmitoyl (16:0) or stearoyl (18:0) CoA (McDonough et al., 1992); a gene encoding a stearoyl-acyl carrier protein delta-9 desaturase from castor (Fox et al. 1993); Δ6- and Δ12-desaturases from the cyanobacteria *Synechocystis* responsible for the conversion of linoleic acid (18:2) to gamma-linolenic acid (18:3 gamma) (Reddy et al. 1993); a gene from *Arabidopsis thaliana* that encodes an omega-3 desaturase (Arondel et al. 1992)); plant Δ9-desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al., (1993), for a disclosure of the nucleotide sequence of an *Aspergillus niger* phytase gene. In corn, this, for example, could be accomplished by cloning and then reintroducing DNA associated with the single allele which is responsible for corn mutants characterized by low levels of phytic acid. See Raboy et al., (1990).

A number of genes are known that may be used to alter carbohydrate metabolism. For example, plants may be transformed with a gene coding for an enzyme that alters the branching pattern of starch. See Shiroza et al., (1988) (nucleotide sequence of *Streptococcus mutants* fructosyltransferase gene), Steinmetz et al., (1985) (nucleotide sequence of *Bacillus subtilis* levansucrase gene), Pen et al., (1992) (production of transgenic plants that express *Bacillus lichenifonnis* α-amylase), Elliot et al., (1993) (nucleotide sequences of tomato invertase genes), Sergaard et al., (1993) (site-directed mutagenesis of barley α-amylase gene), and Fisher et al., (1993) (maize endosperm starch branching enzyme II). The Z10 gene encoding a 10 kD zein storage protein from maize may also be used to alter the quantities of 10 kD Zein in the cells relative to other components (Kirihara et al., 1988).

G. Origin and Breeding History of an Exemplary Introduced Trait

Provided by the invention are hybrid plant in which one or more of the parents comprise an introduced trait. Such a plant may be defined as comprising a single locus conversion. Exemplary procedures for the preparation of such single locus conversions are disclosed in U.S. patent application Ser. No. 09/772,520, the entire disclosure of which is specifically incorporated herein by reference.

An example of a single locus conversion is 85DGD1. 85DGD1 MLms is a conversion of 85DGD1 to cytoplasmic male sterility. 85DGD1 MLms was derived using backcross methods. 85DGD1 (a proprietary inbred of Monsanto Company) was used as the recurrent parent and MLms, a germplasm source carrying ML cytoplasmic sterility, was used as the nonrecurrent parent. The breeding history of the converted inbred 85DGD1 MLms can be summarized as follows:

| | |
|---|---|
| Hawaii Nurseries Planting Date Apr. 2, 1992 | Made up S-O: Female row 585 male row 500 |
| Hawaii Nurseries Planting Date Jul. 15, 1992 | S-O was grown and plants were backcrossed times 85DGD1 (rows 444 ' 443) |
| Hawaii Nurseries Planting Date Nov. 18, 1992 | Bulked seed of the BC1 was grown and backcrossed times 85DGD1 (rows V3-27 ' V3-26) |
| Hawaii Nurseries Planting Date Apr. 2, 1993 | Bulked seed of the BC2 was grown and backcrossed times 85DGD1 (rows 37 ' 36) |
| Hawaii Nurseries Planting Date Jul. 14, 1993 | Bulked seed of the BC3 was grown and backcrossed times 85DGD1 (rows 99 ' 98) |
| Hawaii Nurseries Planting Date Oct. 28, 1993 | Bulked seed of BC4 was grown and backcrossed times 85DGD1 (rows KS-63 ' KS-62) |
| Summer 1994 | A single ear of the BC5 was grown and backcrossed times 85DGD1 (MC94-822 ' MC94-822-7) |
| Winter 1994 | Bulked seed of the BC6 was grown and backcrossed times 85DGD1 (3Q-1 ' 3Q-2) |
| Summer 1995 | Seed of the BC7 was bulked and named 85DGD1 MLms. |

As described, techniques for the production of corn plants with added traits are well known in the art (see, e.g., Poehlman et al., 1995; Fehr, 1987; Sprague and Dudley, 1988). A non-limiting example of such a procedure one of skill in the art could use for preparation of a hybrid corn plant CH675395 comprising an added trait is as follows:

(a) crossing a parent of hybrid corn plant CH675395 such as I325350 and/or CV646435 to a second (nonrecurrent) corn plant comprising a locus to be converted in the parent;

(b) selecting at least a first progeny plant resulting from the crossing and comprising the locus;

(c) crossing the selected progeny to the parent line of corn plant CH675395;

(d) repeating steps (b) and (c) until a parent line of variety CH675395 is obtained comprising the locus; and (e) crossing the converted parent with the second parent to produce hybrid variety CH675395 comprising a desired trait.

Following these steps, essentially any locus may be introduced into hybrid corn variety CH675395. For example, molecular techniques allow introduction of any given locus, without the need for phenotypic screening of progeny during the backcrossing steps.

PCR and Southern hybridization are two examples of molecular techniques that may be used for confirmation of the presence of a given locus and thus conversion of that locus. The techniques are carried out as follows: Seeds of progeny plants are grown and DNA isolated from leaf tissue (see Sambrook et al., 2001; Shure et al. 1983). Approximately one gram of leaf tissue is lyophilized overnight in 15 ml polypropylene tubes. Freeze-dried tissue is ground to a power in the tube using a glass rod. Powdered tissue is mixed thoroughly with 3 ml extraction buffer (7.0 urea, 0.35 M NaCl, 0.05 M Tris-HCI pH 8.0, 0.01 M EDTA, 1% sarcosine). Tissue/buffer homogenate is extracted with 3 ml phenol/chloroform. The aqueous phase is separated by centrifugation, and precipitated twice using 1/10 volume of 4.4 M ammonium acetate pH 5.2, and an equal volume of isopropanol. The precipitate is washed with 75% ethanol and resuspended in 100-500 μl TE (0.01 M Tris-HCI, 0.001 M EDTA, pH 8.0). The DNA may then be screened as desired for presence of the locus.

For PCR, two hundred to 1000 ng genomic DNA from the progeny plant being screened is added to a reaction mix containing 10 mM Tris-HCl pH 8.3, 1.5 mM $MgCl_2$, 50 mM KCl, 0.1 mg/ml gelatin, 200 µM each dATP, dCTP, dGTP, dTTP, 20% glycerol, 2.5 units Taq DNA polymerase and 0.5 µM each of forward and reverse DNA primers that span a segment of the locus being converted. The reaction is run in a thermal cycling machine 3 minutes at 94 C, 39 repeats of the cycle 1 minute at 94 C, 1 minute at 50 C, 30 seconds at 72 C, followed by 5 minutes at 72 C. Twenty µl of each reaction mix is run on a 3.5% NuSieve gel in TBE buffer (90 mM Tris-borate, 2 mM EDTA) at 50V for two to four hours. The amplified fragment is detected using an agarose gel. Detection of an amplified fragment corresponding to the segment of the locus spanned by the primers indicates the presence of the locus.

For Southern analysis, plant DNA is restricted, separated in an agarose gel and transferred to a Nylon filter in 10×SCP (20 SCP: 2M NaCl, 0.6 M disodium phosphate, 0.02 M disodium EDTA) according to standard methods (Southern, 1975). Locus DNA or RNA sequences are labeled, for example, radioactively with $^{32}P$ by random priming (Feinberg & Vogelstein, 1983). Filters are prehybridized in 6×SCP, 10% dextran sulfate, 2% sarcosine, and 500 µg/ml denatured salmon sperm DNA. The labeled probe is denatured, hybridized to the filter and washed in 2×SCP, 1% SDS at 65° for 30 minutes and visualized by autoradiography using Kodak XAR5 film. Presence of the locus is indicated by detection of restriction fragments of the appropriate size.

VI. Tissue Cultures and In Vitro Regeneration of Corn Plants

A further aspect of the invention relates to tissue cultures of the corn plant designated CH675395. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, ears, cobs, leaves, husks, stalks, roots, root tips, anthers, silk, and the like. In a preferred embodiment, the tissue culture comprises embryos, protoplasts, meristematic cells, pollen, leaves or anthers derived from immature tissues of these plant parts. Means for preparing and maintaining plant tissue cultures are well known in the art (U.S. Pat. No. 5,538,880; and U.S. Pat. No. 5,550,318, each incorporated herein by reference in their entirety). By way of example, a tissue culture comprising organs such as tassels or anthers has been used to produce regenerated plants (U.S. Pat. No. 5,445,961 and U.S. Pat. No. 5,322,789; the disclosures of which are incorporated herein by reference).

One type of tissue culture is tassel/anther culture. Tassels contain anthers which in turn enclose microspores. Microspores develop into pollen. For anther/microspore culture, if tassels are the plant composition, they are preferably selected at a stage when the microspores are uninucleate, that is, include only one, rather than 2 or 3 nuclei. Methods to determine the correct stage are well known to those skilled in the art and include mitramycin fluorescent staining (Pace et al., 1987), trypan blue (preferred) and acetocarmine squashing. The mid-uninucleate microspore stage has been found to be the developmental stage most responsive to the subsequent methods disclosed to ultimately produce plants.

Although microspore-containing plant organs such as tassels can generally be pretreated at any cold temperature below about 25° C., a range of 4 to 25° C. is preferred, and a range of 8 to 14° C. is particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture. Exemplary methods of microspore culture are disclosed in, for example, U.S. Pat. No. 5,322,789 and U.S. Pat. No. 5,445,961, the disclosures of which are specifically incorporated herein by reference.

Although not required, when tassels are employed as the plant organ, it is generally preferred to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When one elects to employ tassels directly, tassels are preferably pretreated at a cold temperature for a predefined time, preferably at 10° C. for about 4 days. After pretreatment of a whole tassel at a cold temperature, dissected anthers are further pretreated in an environment that diverts microspores from their developmental pathway. The function of the preculture medium is to switch the developmental program from one of pollen development to that of embryoid/callus development. An embodiment of such an environment in the form of a preculture medium includes a sugar alcohol, for example mannitol or sorbitol, inositol or the like. An exemplary synergistic combination is the use of mannitol at a temperature of about 10° C. for a period ranging from about 10 to 14 days. In a preferred embodiment, 3 ml of 0.3 M mannitol combined with 50 mg/l of ascorbic acid, silver nitrate, and colchicine is used for incubation of anthers at 10° C. for between 10 and 14 days. Another embodiment is to substitute sorbitol for mannitol. The colchicine produces chromosome doubling at this early stage. The chromosome doubling agent is preferably only present at the preculture stage.

It is believed that the mannitol or other similar carbon structure or environmental stress induces starvation and functions to force microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in $10^4$ microspores, have resulted from using these methods.

To isolate microspores, an isolation media is preferred. An isolation media is used to separate microspores from the anther walls while maintaining their viability and embryogenic potential. An illustrative embodiment of an isolation media includes a 6% sucrose or maltose solution combined with an antioxidant such as 50 mg/l of ascorbic acid, 0.1 mg/l biotin, and 400 mg/l of proline, combined with 10 mg/l of nicotinic acid and 0.5 mg/l $AgNO_3$. In another embodiment, the biotin and proline are omitted.

An isolation media preferably has a higher antioxidant level where it is used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably, from about 50 mg/l to about 100 mg/l.

One can find particular benefit in employing a support for the microspores during culturing and subculturing. Any support that maintains the cells near the surface can be used. An illustrative embodiment of a solid support is a TRAN-SWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as an approximately circular support material which is capable of floating slightly above the bottom of a tissue culture vessel, for example, a petri dish, of about a 60 or 100 mm size, although any other laboratory tissue culture vessel will suffice. In an illustrative embodiment, a raft is about 55 mm in diameter.

Culturing isolated microspores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids ultimately to full strength medium containing activated charcoal and solidified with, for example, GELRITE™ (solidifying agent).

The liquid medium passes through the mesh while the microspores are retained and supported at the medium-air interface. The surface tension of the liquid medium in the petri dish causes the raft to float. The liquid is able to pass through the mesh; consequently, the microspores stay on top. The mesh remains on top of the total volume of liquid medium.

The culture vessels can be further defined as either (1) a bilayer 60 mm petri plate wherein the bottom 2 ml of medium are solidified with 0.7% agarose overlaid with 1 mm of liquid containing the microspores; (2) a nylon mesh raft wherein a wafer of nylon is floated on 1.2 ml of medium and 1 ml of isolated microspores is pipetted on top; or (3) TRAN-SWELL® plates wherein isolated microspores are pipetted onto membrane inserts which support the microspores at the surface of 2 ml of medium.

Examples of processes of tissue culturing and regeneration of corn are described in, for example, European Patent Application 0 160 390, Green and Rhodes (1982) and Duncan et al. (1985), Songstad et al. (1988), Rao et al. (1986), Conger et al. (1987), PCT Application WO 95/06128, Armstrong and Green, 1985; Gordon-Kamm et al., 1990, and U.S. Pat. No. 5,736,369.

VII. Processes of Preparing Corn Plants and the Corn Plants Produced by Such Crosses The present invention provides processes of preparing novel corn plants and corn plants produced by such processes. In accordance with such a process, a first parent corn plant may be crossed with a second parent corn plant wherein the first and second corn plants are the parent lines of hybrid corn plant variety CH675395, or wherein at least one of the plants is of hybrid corn plant variety CH675395.

Corn plants (*Zea mays* L.) can be crossed by either natural or mechanical techniques. Natural pollination occurs in corn when wind blows pollen from the tassels to the silks that protrude from the tops of the recipient ears. Mechanical pollination can be effected either by controlling the types of pollen that can blow onto the silks or by pollinating by hand. In one embodiment, crossing comprises the steps of:

(a) planting in pollinating proximity seeds of a first and a second parent corn plant, and preferably, seeds of a first inbred corn plant and a second, distinct inbred corn plant;

(b) cultivating or growing the seeds of the first and second parent corn plants into plants that bear flowers;

(c) emasculating flowers of either the first or second parent corn plant, i.e., treating the flowers so as to prevent pollen production, or alternatively, using as the female parent a male sterile plant, thereby providing an emasculated parent corn plant;

(d) allowing natural cross-pollination to occur between the first and second parent corn plants;

(e) harvesting seeds produced on the emasculated parent corn plant; and, where desired, (f) growing the harvested seed into a corn plant, preferably, a hybrid corn plant.

Parental plants are typically planted in pollinating proximity to each other by planting the parental plants in alternating rows, in blocks or in any other convenient planting pattern. Where the parental plants differ in timing of sexual maturity, it may be desired to plant the slower maturing plant first, thereby ensuring the availability of pollen from the male parent during the time at which silks on the female parent are receptive to pollen. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event that plant CH675395 is employed as the male parent, the tassels of the other parental plant are removed from all plants employed as the female parental plant to avoid self-pollination. The detasseling can be achieved manually but also can be done by machine, if desired. Alternatively, when the female parent corn plant comprises a cytoplasmic or nuclear gene conferring male sterility, detasseling may not be required. Additionally, a chemical gametocide may be used to sterilize the male flowers of the female plant. In this case, the parent plants used as the male may either not be treated with the chemical agent or may comprise a genetic factor which causes resistance to the emasculating effects of the chemical agent. Gametocides affect processes or cells involved in the development, maturation or release of pollen. Plants treated with such gametocides are rendered male sterile, but typically remain female fertile. The use of chemical gametocides is described, for example, in U.S. Pat. No. 4,936,904, the disclosure of which is specifically incorporated herein by reference in its entirety. Furthermore, the use of Roundup herbicide in combination with glyphosate tolerant corn plants to produce male sterile corn plants is disclosed in PCT Publication WO 98/44140.

Following emasculation, the plants are then typically allowed to continue to grow and natural cross-pollination occurs as a result of the action of wind, which is normal in the pollination of grasses, including corn. As a result of the emasculation of the female parent plant, all the pollen from the male parent plant is available for pollination because tassels, and thereby pollen bearing flowering parts, have been previously removed from all plants of the plant being used as the female in the hybridization. Of course, during this hybridization procedure, the parental varieties are grown such that they are isolated from other corn fields to minimize or prevent any accidental contamination of pollen from foreign sources. These isolation techniques are well within the skill of those skilled in this art.

Both parental plants of corn may be allowed to continue to grow until maturity or the male rows may be destroyed after flowering is complete. Only the ears from the female parental plants are harvested to obtain seeds of a novel $F_1$ hybrid. The novel $F_1$ hybrid seed produced can then be planted in a subsequent growing season in commercial fields or, alternatively, advanced in breeding protocols for purposes of developing novel inbred lines.

Alternatively, in another embodiment of the invention, one or both first and second parent corn plants can be from variety CH675395. Thus, any corn plant produced using corn plant CH675395 forms a part of the invention. As used herein, crossing can mean selfing, backcrossing, crossing to another or the same variety, crossing to populations, and the like. All corn plants produced using the corn variety CH675395 as a parent are, therefore, within the scope of this invention.

One use of the instant corn variety is in the production of hybrid seed. Any time the corn plant CH675395 is crossed with another, different, corn plant, a corn hybrid plant is produced. As such, hybrid corn plant can be produced by crossing CH675395 with any second corn plant. Essentially any other corn plant can be used to produce a corn plant having corn plant CH675395 as one parent. All that is required is that the second plant be fertile, which corn plants naturally are, and that the plant is not corn variety CH675395.

The goal of the process of producing an $F_1$ hybrid is to manipulate the genetic complement of corn to generate new combinations of genes which interact to yield new or improved traits (phenotypic characteristics). A process of producing an $F_1$ hybrid typically begins with the production of one or more inbred plants. Those plants are produced by repeated crossing of ancestrally related corn plants to try to combine certain genes within the inbred plants.

Corn has a diploid phase which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, in particular leading to reduced vigor, less kernels, weak and/or poor growth, production of inbred plants is an unpredictable and arduous process. Under some conditions, heterozygous advantage at some loci effectively bars perpetuation of homozygosity.

A single cross hybrid corn variety is the cross of two inbred plants, each of which has a genotype which complements the genotype of the other. Typically, $F_1$ hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two F1 hybrids are crossed again (A×B)×(C×D).

Thousands of corn varieties are known to those of skill in the art, any one of which could be crossed with corn plant CH675395 to produce a hybrid plant. For example, the U.S. Patent & Trademark has issued more than 300 utility patents for corn varieties. Estimates place the number of different corn accessions in genebanks around the world at around 50,000 (Chang, 1992). The Maize Genetics Cooperation Stock Center, which is supported by the U.S. Department of Agriculture, has a total collection approaching 80,000 individually pedigreed samples (//w3.ag.uiuc.edu/maize-coop/mgc-info.html).

When the corn plant CH675395 is crossed with another plant to yield progeny, it can serve as either the maternal or paternal plant. For many crosses, the outcome is the same regardless of the assigned sex of the parental plants. However, due to increased seed yield and production characteristics, it may be desired to use one parental plant as the maternal plant. Some plants produce tighter ear husks leading to more loss, for example due to rot. There can be delays in silk formation which deleteriously affect timing of the reproductive cycle for a pair of parental inbreds. Seed coat characteristics can be preferable in one plant. Pollen can be shed better by one plant. Other variables can also affect preferred sexual assignment of a particular cross.

The development of a hybrid corn variety involves three steps: (1) the selection of plants from various germplasm pools; (2) the selfing of the selected plants for several generations to produce a series of inbred plants, which, although different from each other, each breed true and are highly uniform; and (3) crossing the selected inbred plants with unrelated inbred plants to produce the hybrid progeny ($F_1$). During the inbreeding process in corn, the vigor of the plants decreases. Vigor is restored when two unrelated inbred plants are crossed to produce the hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not generally beneficial for farmers to save seed of $F_1$ hybrids. Rather, farmers purchase $F_1$ hybrid seed for planting every year.

The development of inbred plants generally requires at least about 5 to 7 generations of selfing. Inbred plants are then cross-bred in an attempt to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids. FACT, an acronym for Field Analysis Comparison Trial (strip trials), is an on-farm experimental testing program employed by Monsanto Company to perform the final evaluation of the commercial potential of a product.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and generally are commercially successful. That is, comparisons of experimental hybrids are made to competitive hybrids to determine if there was any advantage to further development of the experimental hybrids. Examples of such comparisons are presented hereinbelow. After FACT testing is complete, determinations may be made whether commercial development should proceed for a given hybrid.

The present invention provides a genetic complement of the hybrid corn plant variety designated CH675395. As used herein, the phrase "genetic complement" means an aggregate of nucleotide sequences, the expression of which defines the phenotype of a corn plant or a cell or tissue of that plant. By way of example, a corn plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus. A preferred type of genetic marker for use with the invention is simple sequence repeats (SSRs), although potentially any other type of genetic marker could be used, for example, restriction fragment length polymorphisms (RFLPs), amplified fragment length polymorphisms (AFLPs), single nucleotide polymorphisms (SNPs), and isozymes.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 5,530,191; U.S. Pat. No. 3,710,511; U.S. Pat. No. 3,861,709; U.S. Pat. No. 4,654,465; U.S. Pat. No. 4,727,219 U.S. Pat. No. 4,769,061; U.S. Pat. No. 4,810,648; U.S. Pat. No. 4,936,904; U.S. Pat. No. 4,940,835; U.S. Pat. No. 4,975,374; U.S. Pat. No. 5,302,532; U.S. Pat. No. 5,322,789; U.S. Pat. No. 5,371,003; U.S. Pat. No. 5,384,253; U.S. Pat. No. 5,445,961; U.S. Pat. No. 5,464,765; U.S. Pat. No. 5,538,880; U.S. Pat. No. 5,550,318; U.S. Pat. No. 5,591,616; U.S. Pat. No. 5,625,132; U.S. Pat. No. 5,684,242; U.S. Pat. No. 5,689,041; U.S. Pat. No. 5,736,369; U.S. Pat. No. 5,736,369; U.S. Pat. No. 5,741,684

Abe et al., *J. Biol. Chem.*, 262:16793, 1987.
Armstrong and Green, *Planta*, 164:207-214, 1985.
Arondel et al., *Science*, 258(5086):1353-1355 1992.
Beachy et al., *Ann. Rev. Phytopathol.*, 28:451, 1990.
Chang, In *Plant Breeding in the 1990s*, Stalker and Murphy (Eds.), Wallingford, U.K., CAB International, 17-35, 1992.
Conger et al., *Plant Cell Reports*, 6:345-347, 1987.
DeGreef et al., *Bioflechnology*, 7:61, 1989.
Duncan et al., *Planta*, 165:322-332, 1985.
Elliot et al., *Plant Molec. Biol.*, 21:515, 1993.
European Appln. 0160390
European Appln. 0242246
European Appln. 0333033
European Appln. 0616644
European Appln. 672752
Fehr, In: *Principles of Cultivar Development*, 1:360-376, 1987.
Feinberg & Vogelstein, *Anal. Biochem.*, 132(1):6-13, 1983.
Fisher et al., *Plant Physiol.*, 102:1045, 1993.
Fox et al. *Proc. Natl. Acad. Sci. USA*, 90(6):2486-2490, 1993.
Geiser et al., *Int. J. Health Serv.*, 16(1):105-120, 1986.
Gleen et al., *Plant Molec. Biology*, 18:1185-1187, 1992.
Gordon-Kamm et al., *The Plant Cell*, 2:603-618, 1990.
Green and Rhodes, In: *Maize for Biological Research*, 367-372, 1982.
Hammock et al., *Nature*, 344:458, 1990.
Hayes et al., *Biochem. J.*, 285(Pt 1):173-180, 1992.
Huub et al., *Plant Molec. Biol.*, 21:985, 1993.
Jones et al., *Science*, 266:7891, 1994.
Kirihara et al., *Gene*, 71(2):359-370, 1988.
Knutzon et al., *Proc. Natl. Acad. Sci. USA*, 89:2624, 1992.
Lee et al., *EMBO J.*, 7:1241, 1988.
Logemann et al., *Biotechnology*, 10:305, 1992.
Marshall et al., *Theor. Appl. Genet.*, 83:4:35, 1992.
Martin et al., *Science*, 262: 1432, 1993.
McDonough et al., *J. Biol. Chem.*, 267(9):5931-5936, 1992.
Miki et al., *Theor. Appl. Genet.*, 80:449, 1990.
Mindrinos et al., *Cell*, 78(6):1089-1099, 1994.
Omirulleh et al., *Plant Mol. Biol.*, 21(3):415-428, 1993.
Pace et al., *Theoretical and Applied Genetics*, 73:863-869, 1987.
PCT Appln. US93/06487
PCT Appln. WO 91/13972
PCT Appln. WO 95/06128
PCT Appln. WO 98/44140
Pen et al., *Biotechnology*, 10:292, 1992.
Poehlman et al., In: *Breeding Field Crops*, 4th Ed., Iowa State University Press, Ames, IA, pp 132-155 and 321-344, 1995.
Przibila et al., *Plant Cell*, 3:169, 1991.
Raboy et al., Plant Physiol., 124(1):355-368.
Rao et al., *Maize Genetics Cooperation Newsletter*, 60, 1986.
Reddy et al., Plant Mol. Biol., 22(2):293-300, 1993.
Sambrook et al., In: *Molecular cloning*, Cold Spring Harbor Laboratory Press, Cold Spring Harbor, N.Y., 2001.
Sergaard et al., *J. Biol. Chem.*, 268:22480, 1993.
Shiroza et al., *J. BacteoL.*, 170:810, 1988.
Shure et al., *Cell*, 35(1):225-233, 1983.
Songstad et al., *Plant Cell Reports*, 7:262-265, 1988.
Sprague and Dudley (eds.), In: *Corn and Corn Improvement*, 3rd Ed., Crop Science of America, Inc., and Soil Science of America, Inc., Madison Wis. 881-883; 901-918, 1988.
Steinmetz et al., *Mol. Gen. Genet.*, 20:220, 1985.
Sumitani et al., *Biosci. Biotech. Biochem.*, 57:1243, 1993.
Tavladoraki et al., *Nature*, 366:469, 1993.
Taylor et al., Seventh Int'l Symposium on Molecular Plant-Microbe Interactions, Edinburgh, Scotland, Abstract W97, 1994.
Van Damme et al., *Plant Molec. Biol.*, 24:25, 1994.
Van Hartingsveldt et al., *Gene*, 127:87, 1993.
Wang et al., *Science*, 280:1077-1082, 1998.
Williams et al., *Nucleic Acids Res.*, 18:6531-6535, 1990.

What is claimed is:

1. A seed of the hybrid corn variety CH675395, produced by crossing a first plant of variety I325350 with a second plant of variety CV646435, wherein representative seed of said varieties I325350 and CV646435 have been deposited under ATCC Accession numbers PTA-7866 and PTA-10243, respectively.

2. A plant of the hybrid corn variety CH675395 grown from the seed of claim 1.

3. A plant part of the plant of claim 2.

4. The plant part of claim 3, further defined as an ear, ovule, pollen or cell.

5. A tissue culture of cells of the plant of claim 2.

6. The tissue culture of claim 5, wherein cells of the tissue culture are from a tissue selected from the group consisting of leaf, pollen, embryo, root, root tip, anther, silk, flower, kernel, ear, cob, husk, stalk and meristem.

7. The seed of claim 1, wherein one or both of the first and second plants further comprises a transgene.

8. The seed of claim 7, wherein the transgene confers a trait selected from the group consisting of male sterility, herbicide tolerance, insect resistance, disease resistance, waxy starch, modified fatty acid metabolism, modified phytic acid metabolism, modified carbohydrate metabolism and modified protein metabolism.

9. The seed of claim 7, wherein the first and second plants each comprise a different transgene.

10. The seed of claim 1, wherein one or both of the first and second plants further comprises a single locus conversion.

11. The seed of claim 10, wherein the single locus conversion confers a trait selected from the group consisting of male sterility, herbicide tolerance, insect resistance, disease resistance, waxy starch, modified fatty acid metabolism, modified phytic acid metabolism, modified carbohydrate metabolism and modified protein metabolism.

12. A method of producing hybrid corn seed comprising crossing a plant of variety I325350 with a plant of variety CV646435, wherein representative seed of variety I325350 and variety CV646435 have been deposited under ATCC Accession numbers PTA-7866 and PTA-10243, respectively.

13. The method of claim 12, defined as comprising pollinating a plant of inbred variety I325350 with pollen from a plant of variety CV646435.

14. The method of claim 12, defined as comprising pollinating a plant of inbred variety CV646435 with pollen from a plant of variety I325350.

15. A method for producing corn grain comprising growing the plant of claim 2 until grain is produced and collecting the grain.

16. A method of introducing a heritable trait into hybrid corn variety CH675395 comprising the steps of:
(a) crossing a first plant of a first inbred corn variety selected from the group consisting of variety I325350 and variety CV646435 with another corn plant that heritably carries the trait to produce progeny plants, at least some of which heritably carry the trait, wherein representative samples of seed of variety I325350 and variety CV646435 have been deposited under ATCC Accession numbers PTA-7866 and PTA-10243, respectively;
(b) selecting progeny plants that heritably carry the trait;
(c) crossing selected progeny plants with another plant of the first inbred corn variety to produce next-generation progeny plants at least some of which heritably carry the trait;
(d) selecting next-generation progeny plants that heritably carry the trait and exhibit morphological and physiological characteristics of the first inbred corn variety;
(e) repeating steps (c) and (d) three or more times to produce at least a first selected progeny plant that heritably carries the trait and exhibits essentially all of the morphological and physical characteristics of the inbred corn variety; and
(f) crossing a progeny plant of step (e) with a plant of the other inbred corn variety of the group consisting of I325350 and CV646435 to produce a plant comprising the trait and essentially all of the characteristics of hybrid corn variety CH675395 when grown under the same environmental conditions.

17. The method of claim 16, wherein the trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

18. The method of claim 17, further comprising repeating steps (a)-(f) at least once to introduce at least a second trait into hybrid corn variety CH675395, wherein the second trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

19. A plant produced by the method of claim 16.

20. A method of introducing a desired trait into hybrid corn variety CH675395 comprising the steps of:
(a) introducing a transgene conferring the trait into a variety selected from the group consisting of I325350 and CV646435 to produce a transgenic plant heritably carrying the trait; and
(b) crossing the transgenic plant or an isogenic progeny plant thereof with a plant of the other inbred corn variety to produce seed of the hybrid corn variety CH675395 that heritably carries and expresses the transgene and otherwise has essentially all of the morphological and physiological characteristics of hybrid corn variety CH675395 when grown under the same environmental conditions.

21. The method of claim 20, wherein the desired trait selected from the group consisting of male sterility, herbicide tolerance, insect resistance, disease resistance, waxy starch, modified fatty acid metabolism, modified phytic acid metabolism, modified carbohydrate metabolism and modified protein metabolism.

22. The method of claim 20, further comprising repeating steps (a) and (b) at least once to introduce at least a second trait into hybrid corn variety CH675395, wherein the second trait is selected from the group consisting of male sterility, herbicide tolerance, insect resistance, disease resistance, waxy starch, modified fatty acid metabolism, modified phytic acid metabolism, modified carbohydrate metabolism and modified protein metabolism.

23. A plant produced by the method of claim 20.

24. The plant of claim 23, wherein the plant comprises a trait selected from the group consisting of male sterility, herbicide tolerance, insect resistance, disease resistance, waxy starch, modified fatty acid metabolism, modified phytic acid metabolism, modified carbohydrate metabolism and modified protein metabolism.

25. A method of producing a corn plant derived from the hybrid corn variety CH675395, comprising crossing the plant of claim 2 with a second corn plant to produce a progeny corn plant derived from the hybrid corn variety CH675395.

26. The method of claim 25, further defined as comprising producing an inbred corn plant derived from the hybrid corn variety CH675395, the method comprising the steps of:
(a) crossing the progeny corn plant derived from the hybrid corn variety CH675395 with itself or a second plant to produce a seed of a progeny plant of a subsequent generation;
(b) growing a progeny plant of a subsequent generation from the seed and crossing the progeny plant of a subsequent generation with itself or a second plant; and
(c) repeating steps (a) and (b) for an additional 3-10 generations with sufficient inbreeding to produce an inbred corn plant derived from the hybrid corn variety CH675395.

* * * * *